US006008379A

United States Patent [19]
Benson et al.

[11] Patent Number: 6,008,379
[45] Date of Patent: Dec. 28, 1999

[54] AROMATIC-SUBSTITUTED XANTHENE DYES

[75] Inventors: Scott Conrad Benson, Oakland; Steven Michael Menchen, Fremont; Peter David Theisen, South San Francisco; Krishna Gajanan Upadhya, Union City; Joan Dale Hauser, Oakland, all of Calif.

[73] Assignee: The Perkin-Elmer Corporation, Foster City, Calif.

[21] Appl. No.: 08/942,067

[22] Filed: Oct. 1, 1997

[51] Int. Cl.$^6$ .................................................. C07D 311/82
[52] U.S. Cl. ............................... 549/224; 435/6; 536/26.6
[58] Field of Search ............................... 435/6; 536/26.6; 549/224

[56] References Cited

U.S. PATENT DOCUMENTS

| 5,188,934 | 2/1993 | Menchen et al. . |
| 5,654,419 | 8/1997 | Mathies et al. . |
| 5,750,409 | 5/1998 | Hermann et al. . |

FOREIGN PATENT DOCUMENTS

| 0 252 683 | 1/1988 | European Pat. Off. ........ C07H 21/04 |
| WO 91/07507 | 5/1991 | WIPO .............................. C12Q 1/68 |
| WO 94/05688 | 3/1994 | WIPO ............................ C07H 21/00 |
| WO 97/00967 | 1/1997 | WIPO .............................. C12P 19/34 |

OTHER PUBLICATIONS

Lee et al., Nuc. Acids Res. 20(10):2471–83, Abstract and Xanthylium structure, RN=142975–78–8, 1992.

*Primary Examiner*—Scott W. Houtteman
*Attorney, Agent, or Firm*—Paul D. Grossman; Alex Andrus; Ann M. Cavini Pease

[57] ABSTRACT

A class of aromatic-substituted xanthene compounds useful as fluorescent dyes is disclosed, the compounds having the general structure where $Y_1$ and $Y_2$ taken separately are selected from the group consisting of hydroxyl, oxygen, imminium, linking group and amine, or $Y_1$ taken together with $R_2$ is cyclic imine, or $Y_2$ taken together with $R_3$ is cyclic amine; $R_2$, $R_3$, $R_5$, and $R_7$ taken separately are selected from the group consisting of hydrogen, fluorine, chlorine, lower alkyl, lower alkene, lower alkyne, sulfonate, sulfone, amino, imminium, amido, nitrile, lower alkoxy, phenyl, and linking group; $R_1$ taken separately is selected from the group consisting of phenyl, substituted phenyl, polycyclic aromatic, substituted polycyclic aromatic, linking group and electron-rich heterocycle, or when taken together with $R_7$ is selected from the group consisting of electron-rich heterocycle and indene; $R_4$ taken separately is selected from the group consisting of amino, amido, phenyl, substituted phenyl, polycyclic aromatic, substituted polycyclic aromatic, indene, linking group and electron-rich heterocycle, or when taken together with $R_5$ is selected from the group consisting of phenyl, substituted phenyl, polycyclic aromatic, substituted polycyclic aromatic, indene, and electron-rich heterocycle; and $R_6$ is selected from the group consisting of acetylene, lower alkyl, lower alkene, cyano, phenyl, substituted phenyl, and heterocyclic aromatic. In another aspect, the invention includes methods for synthesizing the above dye compounds and intermediates. In yet another aspect, the present invention includes reagents labeled with the asymmetric benzoxanthene dye compounds, including deoxynucleotides, dideoxynucleotides, phosphoramidites, and polynucleotides. In an additional aspect, the invention includes methods utilizing such dye compounds and reagents including dideoxy polynucleotide sequencing and fragment analysis methods.

48 Claims, 6 Drawing Sheets

11

12

13

14

15

16

17

18

19 20 21

22 23 24

25 26

32

**36
(Pete)**

**33
(Jeb)**

34

35

AROMATIC-SUBSTITUTED XANTHENE DYES

FIELD OF THE INVENTION

This invention relates generally to fluorescent dye compounds useful as molecular probes. More specifically, this invention relates to aromatic-substituted xanthene dyes useful as fluorescent labeling reagents.

BACKGROUND

The non-radioactive detection of biological analytes utilizing fluorescent labels is an important technology in modem analytical biotechnology. By eliminating the need for radioactive labels, safety is enhanced and the environmental impact of reagent disposal is greatly reduced. Examples of methods utilizing such fluorescent detection methods include DNA sequencing, oligonucleotide probe methods, detection of polymerase-chain-reaction products, immunoassays, and the like.

In many important applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by employing spectrally distinguishable fluorescent labels, the number of reaction tubes may be reduced thereby simplifying experimental protocols and facilitating the manufacturing of application-specific kits. In the case of automated DNA sequencing, multicolor fluorescent labeling allows for the analysis of multiple bases in a single lane thereby increasing throughput over single-color methods and reducing uncertainties associated with inter-lane electrophoretic mobility variations.

Multi-color fluorescent detection imposes five severe constraints on the selection of dye labels, particularly for applications requiring a single excitation light source, an electrophoretic separation, and/or treatment with enzymes, e.g., automated fluorescence-based DNA sequencing. First, it is difficult to find a set of dyes whose emission spectra are spectrally resolved, since the typical emission band half-width for organic fluorescent dyes is about 40–80 nanometers (nm) and the width of available spectrum is limited by the excitation light source. Second, even if dyes with non-overlapping emission spectra are found, the set may still not be suitable if the respective fluorescent efficiencies are too low. Third, when several fluorescent dyes are used concurrently, simultaneous excitation becomes difficult because the absorption bands of the dyes are widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like.

SUMMARY

The present invention relates to the discovery of a class of aromatic-substituted xanthene dye compounds suitable for the creation of sets of spectrally-resolvable fluorescent labels useful for multi-color fluorescent detection. The invention achieves one or more of the following objects depending upon the particular aspect and embodiment employed.

It is an object of the invention to provide a class of aromatic-substituted xanthene dye compounds having red-shifted emission spectra, e.g., emission maxima at a wavelength greater than about 540 nm.

It is a further object of the invention to provide a class of aromatic-substituted xanthene dye compounds suitable for applications requiring multi-color fluorescent detection using a single excitation light source, an electrophoretic separation, and/or treatment with enzymes, e.g., automated fluorescence-based DNA sequencing.

It is another object of the present invention to provide a class of aromatic-substituted xanthene dye compounds wherein the emission spectra of the dyes can be modulated by minor variations in the type of aromatic substituents employed.

It is yet another object of the present invention to provide a class of aromatic-substituted xanthene dye compounds which are substantially brighter than non-aromatic-substituted xanthene dyes.

In a first aspect, the foregoing and other objects of the invention are achieved by an aromatic-substituted xanthene dye compound having the formula

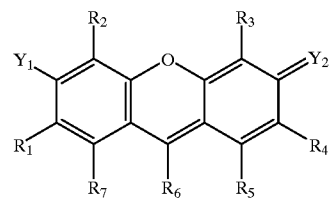

wherein the composition of the variable substituents is as follows. $Y_1$ and $Y_2$ taken separately are selected from the group consisting of hydroxyl, oxygen, imminium, linking group and amine, or $Y_1$ taken together with $R_2$ is cyclic amine, or $Y_2$ taken together with $R_3$ is cyclic imine. $R_2$, $R_3$, $R_5$, and $R_7$ taken separately are selected from the group consisting of hydrogen, fluorine, chlorine, lower alkyl, lower alkene, lower alkyne, sulfonate, sulfone, amino, imminium, amido, nitrile, lower alkoxy, phenyl, and linking group. $R_1$ taken separately is selected from the group consisting of phenyl, substituted phenyl, polycyclic aromatic, substituted polycyclic aromatic, linking group and electron-rich heterocycle, or when taken together with $R_7$ is selected from the group consisting of electron-rich heterocycle and indene. $R_4$ taken separately is selected from the group consisting of hydrogen, fluorine, chlorine, lower alkyl, lower alkene, lower alkyne, sulfonate, sulfone, amino, imminium, amido, nitrile, lower alkoxy, phenyl, linking group, phenyl, substituted phenyl, polycyclic aromatic, substituted polycyclic aromatic, indene, and electron-rich heterocycle, or when taken together with $R_5$ is selected from the group consisting of phenyl, substituted phenyl, polycyclic aromatic, substituted polycyclic aromatic, indene, and electron-rich heterocycle. In the above structure, at least one of $R_4$ and $R_1$ is not linking group. $R_6$ is selected from the group consisting of acetylene, lower alkyl, lower alkene, cyano, phenyl, heterocyclic aromatic, and substituted phenyl having the structure

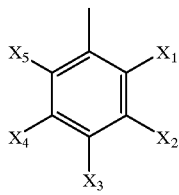

wherein $X_1$–$X_5$ taken separately are hydrogen, chlorine, fluorine, lower alkyl, carboxylic acid, sulfonic acid, —$CH_2OH$, or linking group.

In a second aspect, the invention includes an energy transfer dye comprising a donor dye, and acceptor dye and a linker linking the donor and acceptor dyes. The donor dye is capable of absorbing light at a first wavelength and emitting excitation energy in response, and the acceptor dye is capable of absorbing the excitation energy emitted by the donor dye and fluorescing at a second wavelength in response. The linker serves to facilitate the efficient transfer of energy between the donor dye and the acceptor dye. According to the invention, at least one of the donor dye and acceptor dye is an aromatic-substituted xanthene dye having the structure set forth above.

In a third aspect, the present invention includes a labeled nucleoside/tide having the structure

NUC-DYE wherein NUC is a nucleoside/tide or nucleoside/tide analog and DYE is an aromatic-substituted xanthene dye compound having the structure set forth above. According to the invention, NUC and DYE are connected by a linkage wherein the linkage is attached to DYE at one of positions $R_1$–$R_6$ and wherein if NUC comprises a purine base, the linkage is attached to the 8-position of the purine, if NUC comprises a 7-deazapurine base, the linkage is attached to the 7-position of the 7-deazapurine, and if NUC comprises a pyrimidine base, the linkage is attached to the 5-position of the pyrimidine.

In a fourth aspect, the present invention includes a phosphoramidite compound having the formula:

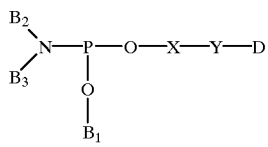

wherein X is a spacer arm; Y is a linkage; $B_1$ is a phosphite ester protecting group; $B_2$ and $B_3$ taken separately are selected from the group consisting of lower alkyl, lower alkene, aryl, and cycloalkyl containing up to 10 carbon atoms; and D is a dye having the structure set forth above. Y and D are linked through a linkage attached to D at one of positions $R_1$–$R_6$.

In a fifth aspect, the invention includes a phosphoramidite compound having the formula

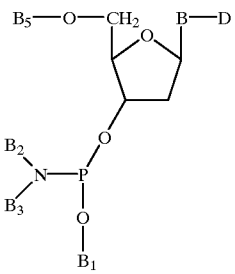

wherein the variable substituents are defined as follows. $B_1$ is a phosphite ester protecting group; $B_2$, and $B_3$ taken separately are selected from the group consisting of lower alkyl, lower alkene, aryl, and cycloalkyl containing up to 10 carbon atoms; $B_5$ is an acid-cleavable hydroxyl protecting group; B is a nucleoside/tide base, and D is a dye compound having the structure set forth above. According to the invention, when B is purine or 7-deazapurine, the sugar moiety is attached at the $N^9$-position of the purine or 7-deazapurine, and when B is pyrimidine, the sugar moiety is attached at the $N^1$-position of the pyrimidine. B and D are linked through a linkage attached to D at one of positions $R_1$–$R_6$. If B is a purine, the linkage is attached to the 8-position of the purine, if B is 7-deazapurine, the linkage is attached to the 7-position of the 7-deazapurine, and if B is pyrimidine, the linkage is attached to the 5-position of the pyrimidine.

In a sixth aspect, the invention includes a method of fragment analysis comprising forming labeled polynucleotide fragments labeled with an aromatic-substituted xanthene dye having the structure set forth above, subjecting the labeled polynucleotide fragments to a size-dependent separation process, e.g., electrophoresis, and detecting the labeled polynucleotide fragments subsequent to the separation process.

These and other objects, features, and advantages of the present invention will become better understood with reference to the following description, drawings, and appended claims.

DETAILED DESCRIPTION OF THE PREFERRED EMBODIMENTS

Figure 1A:
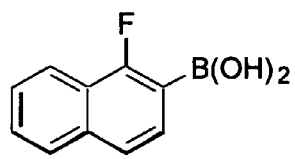
FIGS. 1 A–D show the structure of several intermediates used in the synthesis of the aromatic-substituted xanthene dyes of the present invention and exemplary aromatic-substituted xanthene dye compounds.
Figure 1A:
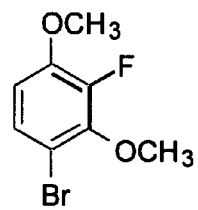
Figure 1A:
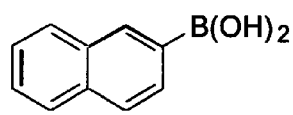
Figure 1A:
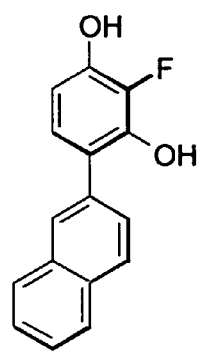
Figure 1A:
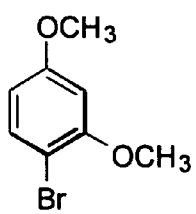
Figure 1A:
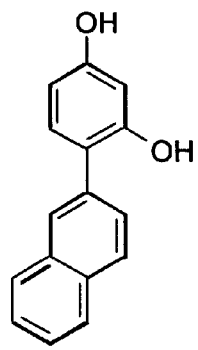
Figure 1A:
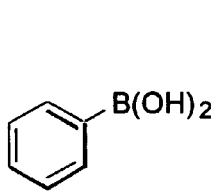
Figure 1A:
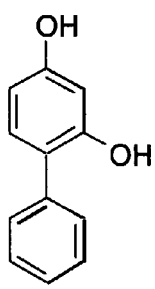
Figure 1B:
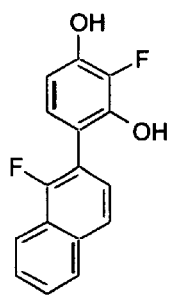
Figure 1B:
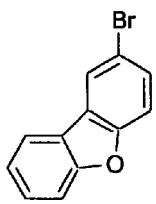
Figure 1B:
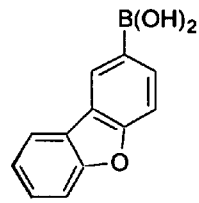
Figure 1B:
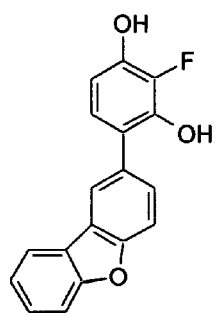
Figure 1B:
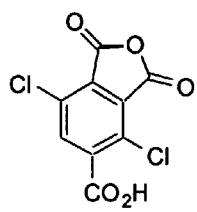
Figure 1B:
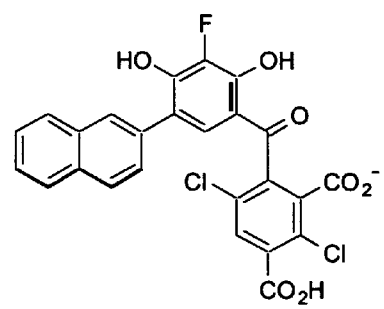
Figure 1B:
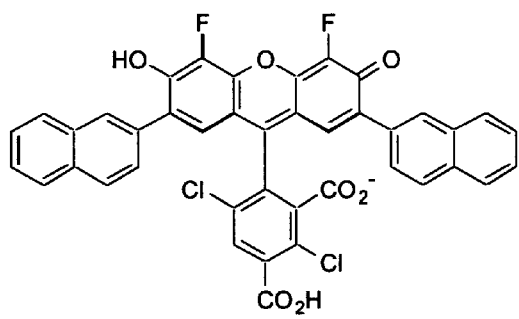
Figure 1B:
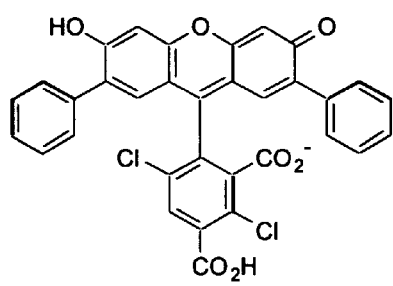
Figure 1C:
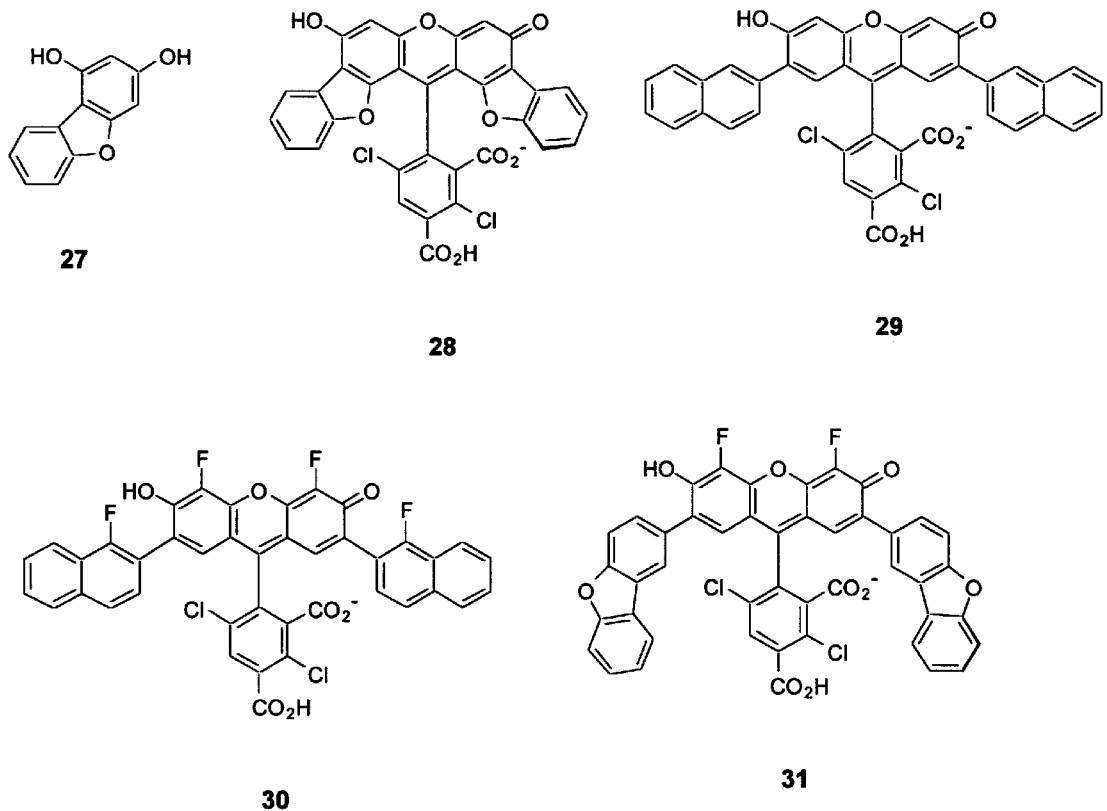
Figure 1D:
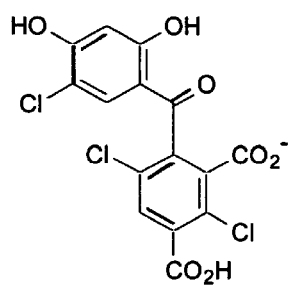
Figure 1D:
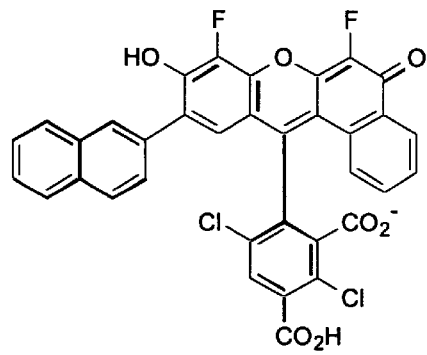
Figure 1D:
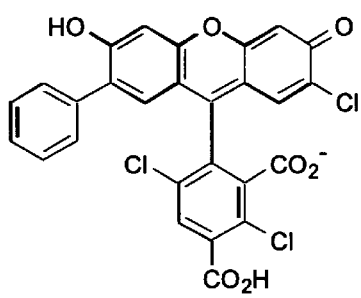
Figure 1D:
Figure 1D:
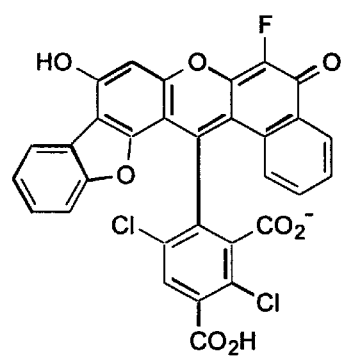

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover all alternatives, modifications, and equivalents, which may be included within the invention as defined by the appended claims.

Generally, the present invention comprises a novel class of aromatic-substituted xanthene dye compounds useful as fluorescent dyes, methods and intermediates for synthesis of such dyes, reagents employing such dyes as molecular labels, and methods utilizing such dyes and reagents in the area of analytical biotechnology. The compounds of the present invention find particular application in the area of fluorescent nucleic acid analysis, e.g., automated fluorescence-based DNA sequencing and fragment analysis, detection of probe hybridization in hybridization arrays, and the like.

I. Definitions

Unless stated otherwise, the following terms and phrases as used herein are intended to have the following meanings:

"Spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, New York, 1985).

"Linking group" means a moiety capable of reacting with a "complementary functionality" attached to a reagent or member of an energy transfer dye pair, such reaction forming a "linkage" connecting the dye to the reagent or member of the energy transfer dye pair. Preferred linking groups include isothiocyanate, sulfonyl chloride, 4,6-dichlorotriazinylamine, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular probes, Inc. (1992). In a particularly preferred embodiment, the linking group is an activated N-hydroxysuccinimidyl (NHS) ester which reacts with an amine complementary functionality, where to form the activated NHS ester, a dye of the invention including a carboxylate linking group is reacted with dicyclohexylcarbodiimide and N-hydroxysuccinimide to form the NHS ester.

"Substituted" as used herein refers to a functional group or moiety in which one or more hydrogen atoms have been replaced with non-hydrogen atoms or moieties. Exemplary substituents include but are not limited to halo, cyano, nitro, sulfo, amido, nitrile and the like.

"Polycyclic aromatic" means aromatic hydrocarbons having multiple ring structures including biaryls and condensed benzenoid hydrocarbons. The biaryls are benzenoid compounds where two or more rings are linked together by a single bond. The parent system of this class is biphenyl. The condensed benzenoid compounds are characterized by two or more benzene rings fused together at ortho positions in such a way that each pair of rings shares two carbons. The simplest members of this group are napthalene, with two rings, and anthracene and phenanthrene, each with three rings.

"Electron-rich heterocycle" means cyclic compounds in which one or more ring atoms are not carbon, i.e., are hetero atoms, and the heteroatoms have unpaired electrons which contribute to a 6-$\pi$ electronic system. Exemplary electron-rich heterocycles include but are not limited to pyrrole, indole, furan, benzofuran, thiophene, benzothiophene and other like structures.

"Lower alkyl" denotes straight-chain and branched hydrocarbon moieties containing from 1 to 8 carbon atoms, e.g., methyl, ethyl, propyl, isopropyl, tert-butyl, isobutyl, sec-butyl, neopentyl, tert-pentyl, and the like. "Lower haloalkyl" denotes a lower substituted alkyl with one or more halogen atom substituents, usually fluorine, chloro, bromo, or iodo.

"Lower alkene" denotes a hydocarbon containing from 1 to 8 carbon atoms wherein one or more of the carbon-carbon bonds are double bonds.

"Lower alkyne" denotes a hydocarbon containing from 1 to 8 carbon atoms wherein one or more of the carbons are bonded with a triple bond.

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position. When the nucleoside base is purine or 7-deazapurine, the sugar moiety is attached at the $N^9$-position of the purine or deazapurine, and when the nucleoside base is pyrimidine, the sugar moiety is attached at the $N^1$-position of the pyrimidine, e.g., Komberg and Baker, *DNA Replication*, 2nd Ed. (Freeman, San Francisco, 1992). The term "nucleotide" as used herein refers to a phosphate ester of a nucleoside, e.g., triphosphate esters, wherein the most common site of esterification is the hydroxyl group attached to the C-5 position of the pentose. The term "nucleoside/tide" as used herein refers to a set of compounds including both nucleosides and nucleotides. "Analogs" in reference to nucleosides/tides include synthetic analogs having modified base moieties, modified sugar moieties and/or modified phosphate moieties, e.g. described generally by Scheit, *Nucleotide Analogs* (John Wiley, New York, 1980). Phosphate analogs comprise analogs of phosphate wherein the phosphorous atom is in the +5 oxidation state and one or more of the oxygen atoms is replaced with a non-oxygen moiety, exemplary analogs including phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present. Exemplary base analogs include but are not limited to 2,6-diaminopurine, hypoxanthine, pseudouridine, C-5-propyne, isocytosine, isoguanine, 2-thiopyrimidine, and other like analogs. Exemplary sugar analogs include but are not limited to 2'-modifications where the 2'-position is hydrogen, hydroxy, alkoxy, e.g., methoxy, ethoxy, allyloxy, isopropoxy, butoxy, isobutoxy and phenoxy, amino or alkylamino, fluoro, chloro and bromo. The term "labeled nucleoside/tide" refers to nucleosides/tides which are covalently attached to the dye compounds of Formula I through a linkage.

"Polynucleotide" or "oligonucleotide" means linear polymers of natural nucleotide monomers or analogs thereof, including double and single stranded deoxyribonucleotides, ribonucleotides, $\alpha$-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., H, $NH_4$, Na, and the like if such counterions are present. Polynucleotides typically range in size from a few monomeric units, e.g. 8–40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

"Xanthene dye" refers to dyes including the general structure

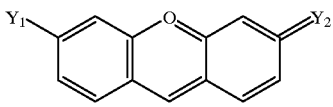

including any and all substituted versions thereof wherein $Y_1$ and $Y_2$ taken separately are selected from the group consisting of hydroxyl, oxygen, imminium, linking group and amine.

II. Aromatic-substituted Xanthene Dye Compounds

A. Structure

In a first aspect, the present invention comprises a novel class of aromatic-substituted xanthene dye compounds having the general structure shown in Formula I immediately below. (Note that any molecular structures provided herein are intended to encompass not only the exact electronic structure presented, but also include all resonant structures and protonation states thereof.)

FORMULA I

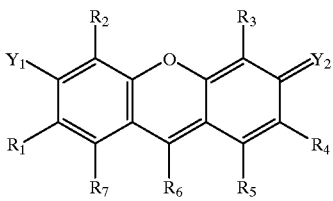

Referring to Formula I, $Y_1$ and $Y_2$ are either individually hydroxyl, oxygen, amine, imminium or linking group. When $Y_1$ is hydroxyl and $Y_2$ is oxygen, the compound is analogous to fluorescein, while when $Y_1$ is amine and $Y_2$ is imminium, the compound is analogous to rhodamine. Preferably $Y_1$ is hydroxyl and $Y_2$ is oxygen.

Moieties $R_1$–$R_6$ are substituents used to modulate various properties of the dyes by modifying the electronic structure of the ground and excited states of the molecule. In particular, varying moieties $R_1$–$R_6$ affects the spectral characteristics, chemical stability, and photostability of the compounds. For example, it has been observed that if $R_6$ is substituted phenyl, making particular substituents $X_2$ and $X_5$ chlorine leads to narrower emission bands. (See below for the definition of substituents $X_2$ and $X_5$.) Particularly important substituents in the context of the present invention are $R_1$, $R_4$, $R_5$, and $R_7$, especially $R_1$ and $R_4$, where such substituents are aromatic or substituted aromatic groups.

Preferably, substituents $R_2$, $R_3$, $R_5$ and $R_7$ are hydrogen, fluorine, chlorine, lower alkyl, lower alkene, lower alkyne, sulfonate, sulfone, amino, immininium, amido, nitrile, aryl, lower alkoxy, or linking group. In a preferred embodiment of the present invention, $R_2$ and/or $R_3$ are hydrogen, chlorine or fluorine.

The nature of substituents $R_1$, $R_4$, $R_5$ and $R_7$ is particularly important to the present invention as it is these substituent positions at which the most relevant aromatic substitutions are made. In particular, substituent $R_1$ taken separately may be phenyl, substituted phenyl, polycyclic aromatic, substituted polycyclic aromatic, and electron-rich heterocycle. Alternatively, when taken together with $R_7$, the $R_1/R_7$ combination may be electron-rich heterocycle or indene. Substituent $R_4$ taken separately is selected from the group consisting of hydrogen, fluorine, chlorine, lower alkyl, lower alkene, lower alkyne, sulfonate, sulfone, amino, imminium, amido, nitrile, lower alkoxy, phenyl, linking group, amine, phenyl, substituted phenyl, polycyclic aromatic, substituted polycyclic aromatic, indene, and electron-rich heterocycle, or when taken together with $R_5$ is selected from the group consisting of phenyl, substituted phenyl, polycyclic aromatic, substituted polycyclic aromatic, indene, and electron-rich heterocycle;

Substituent $R_6$ may be acetylene, lower alkyl, lower alkene, cyano, phenyl, heterocyclic aromatic, or substituted phenyl having the structure:

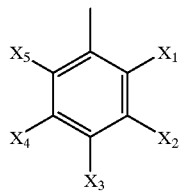

wherein $X_1$–$X_5$ taken separately are hydrogen, chlorine, fluorine, lower alkyl, carboxylic acid, sulfonic acid, —$CH_2OH$, or linking group.

In a particularly preferred embodiment of the present invention in which the mission spectra of the dye is substantially narrower than otherwise substituted dyes, $R_6$ is substituted phenyl, e.g., Menchen et al, U.S. Pat. No. 5,188,934. Preferably, the substituted phenyl is substituted such that $X_1$ is carboxylic acid, sulfonic acid, or —$CH_2OH$; $X_2$ and $X_5$ taken separately are hydrogen, chlorine, fluorine, or lower alkyl; and $X_3$ and $X_4$ taken separately are hydrogen, chlorine, fluorine, lower alkyl, carboxylic acid, sulfonic acid, or linking group. More preferably, $X_2$ and $X_5$ are chlorine. In an additional preferred embodiment, one of $X_3$ or $X_4$ is linking group. Preferably, X, is carboxylic acid. In an additional preferred embodiment particularly suited to forming phosphoramidite compounds including the dye compounds of the invention, one of $X_1$ or $X_5$ is a moiety which is capable of forming a cyclic ester or cyclic ether, e.g., carboxylic acid, sulfonic acid, —$CH_2OH$, or any other group that will form a spirocyclic system, i.e., bicyclic compounds having one carbon atom common to both rings, e.g., spiro[4.5]decane.

Several exemplary aromatic-substituted xanthene dye structures are shown in FIG. 1. In compound 26, $R_1$ and $R_4$ are phenyl; in compound 28, $R_1$ taken together with $R_7$ is an electron-rich heterocycle, and $R_4$ taken together with $R_5$ is an electron-rich heterocycle, more specifically both combinations are benzofuran having 2 and 3 positions fused to the xanthene ring; in compound 29, $R_1$ and $R_4$ taken separately are each polycyclic aromatic, more specifically naphthalene; in compound 25 $R_1$ and $R_4$ taken separately are each naphthalene and $R_2$ and $R_3$ taken separately are fluorine; and in compound 35, $R_1$ taken together with $R_7$ is benzofuran having 2 and 3 positions fused to the xanthene ring, $R_3$ is fluorine, and $R_4$ taken together with $R_5$ is phenyl.

B. Synthetic Methods

Figure 2A:
FIGS. 2A–B show a preferred generalized synthetic scheme according to the invention.
Figure 2A:
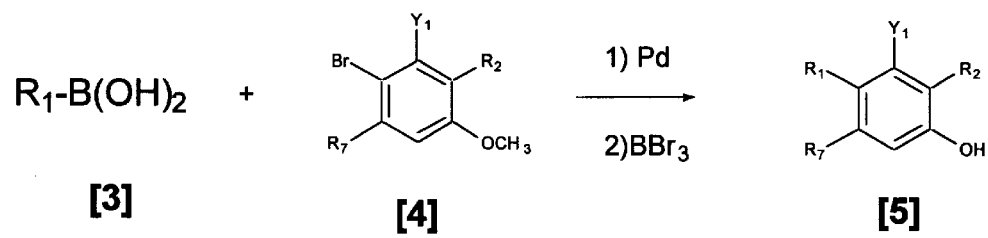
Figure 2B:
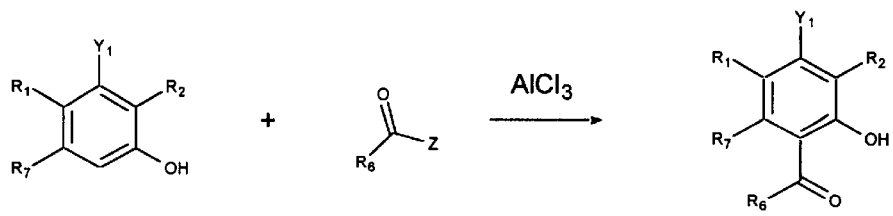
Figure 2B:
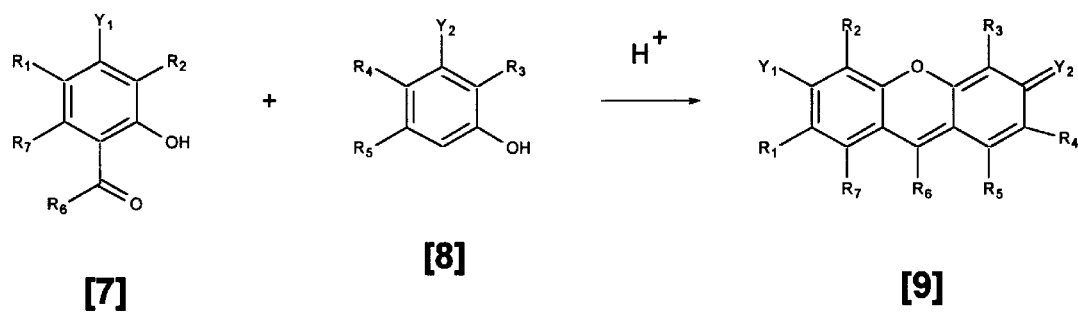

Generally, the aromatic-substituted xanthene dyes of the invention are prepared as follows. See FIGS. 2A–B.

First, one or more functionalized phenol intermediates are prepared by metallating a halogenated phenyl precursor 1, e.g., with an alkyl lithium salt, to form a metallized intermediate 2. The metalated intermediate is then reacted with trimethyl borate followed by hydrolysis to yield the boronic acid 3. The boronic acid 3 then undergos a palladium-catalyzed coupling with bromophenol methyl ether 4 to yield a methylated substituted phenol ether that is subsequently demethylated with boron tribromide to yield the substituted phenol 5. Alternatively, compound 4 may be metallated and converted to its boronic acid, followed by a palladium catalyzed coupling with 1 to ultimately yield 5. The bromide intermediates may also be converted to other intermediates that react with bromides or iodides with palladium catalysis, such as replacing the boronic acid with alkyl tin derivatives.

Unsymmetrical dyes are most readily prepared by first performing a condensation of a first functionalized phenol intermediate 5 with reagent 6 that contains an activated acid such as an acid chloride. The condensation can be performed using a Friedel-Crafts catalyst, such as aluminum chloride, and yields the aromatic ketone 7. Aromatic ketone 7 is then condensed with a second functionalized phenol 8 at elevated temperature, e.g., above 80° C., in the presence of a strong acid, e.g., sulfuric acid, to yield the unsymmetrical aromatic-substituted xanthene dye 9.

Symmetrical aromatic-substituted xanthene dyes are most easily prepared by condensing two equivalents of a substituted phenol intermediate 5 with one equivalent of a reagent 6 that contains an activated acid, e.g., an acid chloride or anhydride, at elevated temperature, e.g., above 80° C., in the presence of a strong acid, e.g., sulfuric acid.

II. Energy Transfer Dyes Incorporating Dye Compounds

In another aspect, the present invention comprises energy transfer dye compounds incorporating the aromatic-substituted xanthene dye compounds of Formula I. Generally, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye, the linker being effective to facilitate efficient energy transfer between the donor and acceptor dyes. A through discussion of the structure, synthesis and use of such energy transfer dyes is provided by Lee et al., U.S. patent application Ser. No. 08/726,462, and Mathies et al., U.S. Pat. No. 5,654,419.

One linker according to the present invention for linking a donor dye to an acceptor dye in an energy transfer fluorescent dye has the general structure

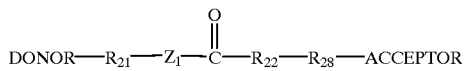

where $R_2$, is a lower alkyl attached to the donor dye, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

In one embodiment of this linker, illustrated below, the linker has the general structure

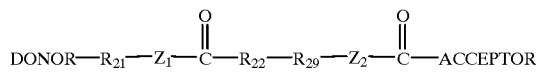

where $R_{21}$ and $R_{22}$ are as detailed above, $Z_1$ and $Z_2$ are each independently either NH, sulfur or oxygen, $R_{29}$ is a lower alkyl, and the terminal carbonyl group is attached to a ring structure of the acceptor dye. In the variation where $Z_2$ is nitrogen, the $C(O)R_{22}R_{29}Z_2$ subunit forms an amino acid subunit. Particular examples of five or six membered rings which may be used as $R_{22}$ in the linker include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene. A preferred embodiment of this linker is where $R_{21}$ and $R_{29}$ are methylene, $Z_1$ and $Z_2$ are NH, and $R_{22}$ is benzene, as shown below.

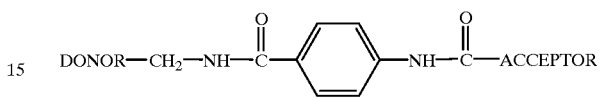

In another preferred embodiment of the energy-transfer-dye aspect of the present invention, the linker attaches to the aromatic-substituted xanthene dye component of the energy transfer dye at the $R_3$ substituent position. In an alternative preferred embodiment, $R_6$ of the aromatic-substituted xanthene dye component of the energy transfer dye is substituted phenyl and the linker attaches to the aromatic-substituted xanthene dye at one of the $X_3$ or $X_4$ substituent positions.

In yet another preferred embodiment of the energy-transfer-dye aspect of the present invention, the first member the dye pair is aromatic-substituted xanthene, and the second member of the dye pair is cyanine, phthalocyanine, squaraine, or aromatic-substituted xanthene having different substitutions than the first member.

III. Reagents Incorporating Dye Compounds

In another aspect, the present invention comprises reagents labeled with the aromatic-substituted xanthene dye compounds of Formula I. Reagents of the invention can be virtually anything to which the dyes of the invention can be attached. Preferably, the dyes are covalently attached to the reagent. Reagents may include but are not limited to proteins, polypeptides, polysaccharides, nucleotides, nucleosides, polynucleotides, lipids, solid supports, organic and inorganic polymers, and combinations and assemblages thereof, such as chromosomes, nuclei, living cells, such as bacteria or other microorganisms, mammalian cells, tissues, and the like.

A. Nucleoside/tide Reagents

A preferred class of labeled reagents comprise nucleoside/tides that incorporate the aromatic-substituted xanthene dyes of the invention. Such nucleoside/tide reagents are particularly useful in the context of labeling polynucleotides formed by enzymatic synthesis, e.g., nucleotide triphosphates used in the context of PCR amplification, Sanger-type polynucleotide sequencing, and nick-translation reactions.

Generally, the structure of the labeled nucleoside/tide reagent is

FORMULA II where NUC is a nucleoside/tide or nucleoside/tide analog and DYE is an aromatic-substituted dye compound of Formula I.

The linkage linking the nucleoside/tide and the dye may be attached to the dye at any one of positions $R_1$–$R_7$. Preferably, the dye and nucleotide are attached through the $R_6$ position of the dye. When the dyes of the invention are synthesized from trimellitic anhydride, $R_6$ is preferably substituted phenyl and the linkage is attached to the dye at one of the $X_3$ or $X_4$ positions of the substituted phenyl, the other position being a hydrogen atom.

When NUC includes a purine base, the linkage between NUC and DYE is attached to the $N^8$-position of the purine, when NUC includes a 7-deazapurine base, the linkage is attached to the $N^7$-position of the 7-deazapurine, and when NUC includes a pyrimidine base, the linkage is attached to the $N^5$-position of the pyrimidine.

Nucleoside labeling can be accomplished using any one of a large number of known nucleoside/tide labeling techniques employing known linkages, linking groups, and associated complementary functionalities. Generally, the linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not adversely affect the fluorescence properties of the dye. Exemplary base labeling procedures suitable for use in connection with the present invention include the following: Gibson et al, *Nucleic Acids Research*, 15:6455–6467 (1987); Gebeyehu et al, *Nucleic Acids Research*, 15: 4513–4535 (1987); Haralambidis et al, *Nucleic Acids Research*, 15: 4856–4876 (1987); Nelson et al., *Nucleosides and Nucleotides*, 5(3): 233–241 (1986); Bergstrom, et al.,*JACS*, 111: 374–375 (1989); U.S. Pat. Nos. 4,855,225, 5,231,191, and 5,449,767.

Preferably, the linkages are acetylenic amido or alkenic amido linkages, the linkage between the dye and the nucleoside/tide base being formed by reacting an activated N-hydroxysuccinimide (NHS) ester of the dye with an alkynylamino- or alkenylamino-derivatized base of a nucleoside/tide. More preferably, the resulting linkage is 3-(carboxy)amino-1-propyn-1-yl having the structure

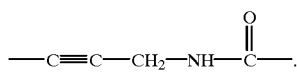

Alternative preferred linkages include substituted propargylethoxyamido linkages having the structure

—C≡C—CH₂OCH₂CH₂NR₃X— wherein X is selected from the group consisting of

where n ranges from 1 to 5,

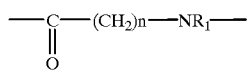

where n ranges from 1 to 5,

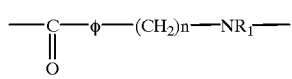

$R_1$ is selected from the group consisting of —H, lower alkyl and protecting group; and $R_3$ is selected from the group consisting of —H and lower alkyl. See Khan et al., U.S. patent application Ser. No. 08/833,854 filed Apr. 10, 1997.

The synthesis of alkynylamino-derivatized nucleosides is taught by Hobbs et al. in European Patent Application No. 87305844.0, and Hobbs et al., *J Org Chem.*, 54: 3420 (1989). Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture is stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Particularly preferred nucleosides/tides of the present invention are shown below in Formula IV wherein

FORMULA IV

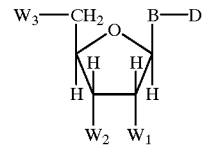

B is a nucleotide base, e.g., uracil, cytosine, deazaadenine, or deazaguanosine; $W_1$ and $W_2$ taken separately are OH or a group capable of blocking polymerase mediated template-directed polymerzation, e.g., H, fluorine and the like; $W_3$ is OH, or mono-, di- or triphosphate or phosphate analog; and D is a dye compound of Formula I. In one particularly preferred embodiment, the nucleotides of the present invention are dideoxynucleotide triphosphates having the structure shown in Formula IV.1 below, including associated counterions if present.

FORMULA IV.1

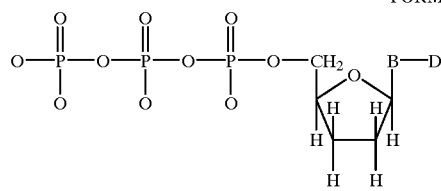

Labeled dideoxy nucleotides such as that shown in Formula IV.1 find particular application as chain terminating agents in Sanger-type DNA sequencing methods utilizing fluorescent detection. In a second particularly preferred embodiment, the nucleotides of the present invention are deoxynucleotide triphosphates having the structure shown in Formula IV.2 below, including associated counterions if present.

FORMULA IV.2

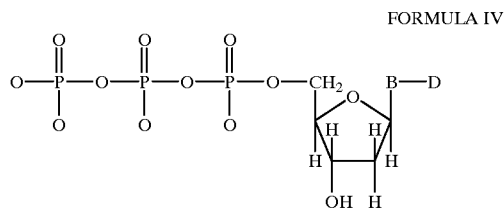

Labeled deoxynucleotides such as that shown in Formula IV.2 find particular application as means for labeling polymerase extension products, e.g., in the polymerase chain reaction or nick-translation.

C. Phosphoramidite Reagents

Another preferred class of reagents comprise phosphoramidite compounds which incorporate the aromatic-substituted xanthene dyes of the invention. Such phosphoramidite reagents are particularly useful for the automated chemical synthesis of polynucleotides labeled with the aromatic-substituted xanthene dyes of the invention. Such phosphoramidite compounds when reacted with a 5'-hydroxyl group of a nucleotide or polynucleotide form a phosphite ester linkage which, in turn, is oxidized to give a phosphate ester linkage, e.g., Caruthers et al., U.S. Pat. Nos. 4,458,066 and 4,415,732.

1. Non-nucleotide Phosphoramidite Reagents: Generally, in one aspect, the phosphoramidite reagents of the invention have the structure of Formula V immediately below,

FORMULA V

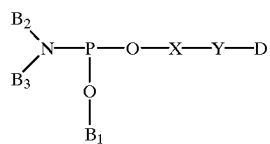

where X is a spacer arm; D is an aromatic-substituted xanthene dye of Formula I or a protected derivative thereof; Y is a linkage formed with a linking group on the dye; $B_1$ is a phosphite ester protecting group, and $B_2$ and $B_3$ taken separately are lower alkyl, lower alkene, lower aryl having between 1 and 8 carbon atoms, aralkyl, or cycloalkyl containing up to 10 carbon atoms. Spacer X and linkage Y may take a variety of forms, however, the structure X-Y must be such that (i) it is stable to DNA synthesis conditions, (ii) does not substantially interfere with oligonucleotide-target hybridization, and (iii) does not quench the fluorescence of the dye to which it is attached, e.g., U.S. Pat. Nos. 5,231,191, 5,258,538, and 4,757,141 and 5,212,304.

Preferably X is linear or cyclic lower alkyl, linear or cyclic substituted lower alkyl, polyethlene oxide, lower aryl having between 1 and 8 carbon atoms, peptide, or polyether. Preferably the linkage Y is amido, sulfonamido, urea, urethane, or thourea. In one particularly preferred embodiment, the linkage Y is amido and the spacer X is linear alkyl having the structure shown below in Formula V.1

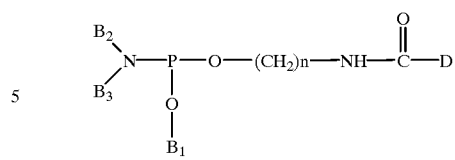

where n ranges from 2 to 30, preferably from 2 to 10, and more preferably from 2 to 6. In a second particularly preferred embodiment, the linkage Y is amido and the spacer X is linear polyethylene oxide having the structure shown below in Formula V.2

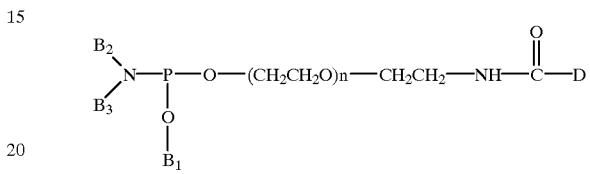

where n is from 2 to 30, preferably from 2 to 10, and more preferably from 2 to 6.

Preferably, $B_2$ and $B_3$ taken together form an alkyl chain containing up to 5 carbon atoms in the principle chain and a total of up to 10 carbon atoms with both terminal valence bonds of said chains being attached to the nitrogen atom. Alternatively, $B_2$ and $B_3$ taken together with the nitrogen atom form a saturated nitrogen heterocycle which contains one or more heteroatoms selected from the group consisting of nitrogen, oxygen, and sulfur. Preferably, $B_2$ and $B_3$ taken separately are isopropyl, t-butyl, isobutyl, or sec-butyl, and $B_2$ and $B_3$ taken together is morphollino.

$B_1$ is a phosphite ester protecting group which prevents unwanted extension of the polynucleotide to which the phosphoramidite is attached. $B_1$ is stable to polynucleotide synthesis conditions yet is able to be removed from the polynucleotide product with a reagent that does not adversely affect the integrity of the polynucleotide or the dye. Preferably, $B_1$ is methyl, $\beta$-cyanoethyl, or 4-nitrophenylethyl.

The linkage linking Y and D is attached to D at one of positions $R_1$–$R_7$. When the dyes of the invention are synthesized from trimelletic anhydride, $R_6$ is preferably substituted phenyl and the linkage is attached to the dye at one of the $X_3$ or $X_4$ positions of the substituted phenyl.

Such phosphoramidite compounds may be synthesized by a variety of known methods. Generally, the synthesis proceeds as follows. Phenolic hydroxyls of the dye are protected with dye-protecting groups that can be removed with a DNA synthesis deprotection agent, e.g., ammonia, ethanolamine, methylamine/ammonium hydroxide mixtures, and mixtures of t-butylamine/water/methanol (1:2:1), e.g., see U.S. Pat. No. 5,231,191. Dyes so protected are referred to herein as "protected derivatives" of the dye. Preferred protecting groups include esters of benzoic acid or pivalic acid. The linking group of the protected dye, e.g., carboxylic acid, is then activated, e.g., with carbodiimide, and reacted with an alcohol linker derivative, e.g., an amino alcohol, e.g., ethanolamine, hexanol amine, or the like, in N,N-dimethylformamide (DMF), or another like aprotic solvent to yield a protected dye with a free alcohol functionality, e.g., alcohol-amide derivative. The free alcohol is then reacted with a phosphitylating agent using standard procedures, e.g., di-(N,N-diisopropylamino) methoxyphosphine in acetonitrile containing catalytic amounts of tetrazole diisopropylamine, to yield the phosphoramidite, e.g., U.S. Pat. No. 5,231,191.

Non-nucleotidic phosphoramidites as shown in Formula V are particularly well suited for labeling the 5'-end of a chemically-synthesized polynucleotide through the sugar-portion of the nucleotide.

2. Nucleotidic Phosphoramidite Reagents: In a second preferred embodiment, the phosphoramidite reagents of the invention have the structure of Formula VI immediately below,

FORMULA VI

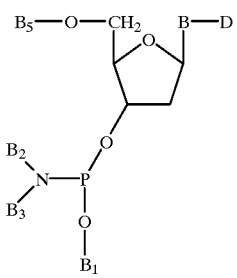

where $B_1$–$B_3$ are as described above, $B_5$ is hydrogen or a hydroxyl protecting group, B is a nucleotide base, and D is an aromatic-substituted xanthene dye of Formula I, or a protected derivative thereof.

When B is purine or 7-deazapurine, the sugar moiety is attached at the $N^9$-position of the purine or deazapurine. Alternatively, when B is pyrimidine, the sugar moiety is attached at the $N^1$-position of the pyrimidine. B and D are linked through a linkage formed by the reaction of a linking group and its complementary functionality as described in detail above. If B is purine, the linkage is attached to the 8-position of the purine, while if B is 7-deazapurine, the linkage is attached to the 7-position of the 7-deazapurine. If B is pyrimidine, the linkage is attached to the 5-position of the pyrimidine.

$B_5$ refers generally to hydrogen or an acid-cleavable hydroxyl protecting group. Preferably, $B_5$ is triphenylmethyl radical and its electron-donating-substituted derivatives, where, as used herein, the term "electron-donating" denotes the tendency of a substituent to release valence electrons to neighboring atoms in the molecule of which it is a part, i.e., it is electropositive with respect to neighboring atoms. Preferably, electron-donating substituents include amino, lower alkyl, lower aryl having between 1 and 8 carbon atoms, lower alkoxy, and the like. More preferably, the electron-donating substituents are methoxy. Exemplary trityls include 4,4'-dimethoxytrityl, i.e. bis(p-anisyl) phenylmethyl, monomethoxytrityl, α-naphthyldiphenylmethyl, tri(p-methoxyphenyl)methyl, and the like. Attachment and cleavage conditions for these and other trityls can be found in Greene and Wuts, *Protective Groups in Organic Synthesis,* 2nd Edition (John Wiley, New York, 1991).

Generally, the nucleotide phosphoramidites of the invention may be synthesized as follows. A nucleoside bearing a hydroxyl protecting group on the 5'-hydroxyl and a protected complementary functionality on the base is selectively deprotected to expose only the complementary functionality. Next, a protected dye (as described above) is activated by converting a linking group into its reactive form. The activated linking group of the dye is then reacted with the complementary functionality of the nucleoside to form the dye labeled nucleoside that bears protecting groups on the 5'-hydroxyl (and on the 2'-hydroxyl for the case of RNA) and on the phenolic groups of the dye. The dye labeled nucleoside is then reacted with a phosphitylating agent as described above to produce the nucleotide phosphoramidite.

In a preferred method where the complementary functionality is amine and the linking group is carboxyl, the synthesis proceeds as follows. A protected nucleoside bearing a hydroxyl protecting group on the 5'-hydroxl, e.g., a trityl group, and a protected amino-nitrogen complementary functionality on the base, is selectively deprotected to expose the amine, such selective deprotection serving to deprotect only the amine functionality without deprotecting the protected 5'-hydroxyl moiety. A protected dye (as described above) is activated by converting a carboxy linking group into its NHS ester with dicyclohexyl carbodiimide and N-hydroxysuccinimide. The NHS ester is reacted with the amino group of the nucleoside to form the dye labeled nucleoside that bears protecting groups on the 5'-hydroxyl (and on the 2'-hydroxyl for the case of RNA) and on the phenolic groups of the dye. The dye labeled nucleoside is then reacted with a phosphitylating agent as described above.

Labeled nucleotide phosphoramidites such as shown in Formula VI are particularly well suited for the internal labeling of chemically-synthesized polynucleotides.

D. Polynucleotide Reagents

Yet another preferred class of reagents of the present invention comprise polynucleotides labeled with the aromatic-substituted xanthene dyes of the invention. Such labeled polynucleotides are useful in a number of important contexts including as DNA sequencing primers, PCR primers, oligonucleotide hybridization probes, oligonucleotide ligation probes, and the like.

In one preferred embodiment, the labeled polynucleotides of the present invention include multiple dyes located such that fluorescence energy transfer takes place between a donor dye and an acceptor dye. Such multi-dye energy-transfer polynucleotides find application as spectrally-tunable sequencing primers, e.g., Ju et al., *Proc. Natl. Acad. Sci. USA* 92: 4347–4351 (1995), and as hybridization probes, e.g., Lee et al. *Nucleic Acids Research,* 21: 3761–3766 (1993).

Labeled polynucleotides may be synthesized either enzymatically, e.g., using a DNA polymerase or ligase, e.g., Stryer, *Biochemistry,* Chapter 24, W.H. Freeman and Company (1981), or by chemical synthesis, e.g., by the phosphoramidite method, the phosphite-triester method, and the like, e.g., Gait, *Oligonucleotide Synthesis,* IRL Press (1990). Labels may be introduced during enzymatic synthesis utilizing labeled nucleotide triphosphate monomers as described above, or introduced during chemical synthesis using labeled non-nucleotide or nucleotide phosphoramidites as described above, or may be introduced subsequent to synthesis.

Generally, if the labeled polynucleotide is made using enzymatic synthesis, the following procedure may be used. A template DNA is denatured and an oligonucleotide primer is annealed to the template DNA. A mixture of deoxynucleotide triphosphates is added to the mixture including dGTP, dATP, dCTP, and dTTP where at least a fraction of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase-mediated strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols,* Innis et al. eds., Academic Press (1990).

Labeled polynucleotides may be chemically synthesized using the phosphoramidite method. Detailed descriptions of the chemistry used to form polynucleotides by the phosphoramidite method are provided elsewhere, e.g., Caruthers et al., U.S. Pat. Nos. 4,458,066 and 4,415,732; Caruthers et al., *Genetic Engineering,* 4: 1–17 (1982); *Users Manual Model* 392 *and* 394 *Polynucleotide Synthesizers,* pages 6-1 through 6-22, Applied Biosystems, Part No. 901237 (1991).

The phosphoramidite method of polynucleotide synthesis is the preferred method because of its efficient and rapid coupling and the stability of the starting materials. The synthesis is performed with the growing polynucleotide chain attached to a solid support, so that excess reagents, which are in the liquid phase, can be easily removed by filtration, thereby eliminating the need for purification steps between synthesis cycles.

The following briefly describes the steps of a typical polynucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dye-labeled phosphoramidites as described above. If the 5'-terminal position of the nucleotide is labeled, a labeled non-nucleotidic phosphoramidite of the invention may be used during the final condensation step. If an internal position of the oligonucleotide is labeled, a labeled nucleotidic phosphoramidite of the invention may be used during any of the condensation steps.

Subsequent to synthesis, the polynucleotide may be labeled at a number of positions including the 5'-terminus, e.g., *Oligonucleotides and Analogs,* Eckstein ed., Chapter 8, IRL Press (1991) and Orgel et al., *Nucleic Acids Research* 11(18): 6513 (1983); U.S. Pat. No. 5,118,800; the phosphodiester backbone, e.g., ibid., Chapter 9; or at the 3'-terminus, e.g., Nelson, *Nucleic Acids Research* 20(23): 6253–6259, and U.S. Pat. Nos. 5,401,837 and 5,141,813. For a through review of oligonucleotide labeling procedures see R. Haugland in *Excited States of Biopolymers,* Steiner ed., Plenum Press, NY (1983).

In one preferred post-synthesis chemical labeling method an oligonuleotide is labeled as follows. A dye including a carboxy linking group is converted to the N-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10–20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA).

The fraction containing the crude labeled oligonucleotide is further purified by reverse phase HPLC employing gradient elution.

IV. Methods Utilizing the Compounds/Reagents of the Invention

The dyes and reagents of the present invention are well suited to any method utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, or that have been distributed among locations in a spatially-addressable hybridization array.

In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphisim detection (AmpFLP) is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

In another such fragment analysis method known as nick translation, a reaction is used to replace unlabeled nucleoside triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing. Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides. Dyes can be linked to a complementary functionality on the 5'-end of the primer, e.g. following the teaching in Fung et al, U.S. Pat. No. 4,757,141; on the base of a primer; or on the base of a dideoxynucleotide, e.g. via the alkynylamino linking groups disclosed by Hobbs et al, supra.

In each of the above fragment analysis methods labeled polynucleotides are preferably separated by electrophoretic procedures, e.g. Gould and Matthews, cited above; Rickwood and Hames, Eds., *Gel Electrophoresis of Nucleic Acids: A Practical Approach*, IRL Press Limited, London, 1981; Osterman, *Methods of Protein and Nucleic Acid Research*, Vol. 1 Springer-Verlag, Berlin, 1984; or U.S. Pat. Nos. 5,374,527, 5,624,800 and/or 5,552,028. Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a denaturing agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology*, 65: 299–305 (1980); Maniatis et al., "Chain Length Determination of Small Double- and Single-Stranded DNA Molecules by Polyacrylamide Gel Electrophoresis," *Biochemistry*, 14: 3787–3794 (1975); Maniatis et al., *Molecular Cloning: A Laboratory Manual*, Cold Spring Harbor Laboratory, New York, pgs. 179–185 (1982); and *ABI PRISM™ 377 DNA Sequencer User's Manual, Rev. A*, January 1995, Chapter 2 (p/n 903433, The Perkin-Elmer Corporation, Foster City, Calif.). The optimal electrophoresis conditions, e.g., polymer concentration, pH, temperature, concentration of denaturing agent, employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Subsequent to electrophoretic separation, the dye-polynucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or an the 532 emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like. Exemplary electrophoresis detection systems are described elsewhere, e.g., U.S. Pat. Nos. 5,543,026; 5,274,240; 4,879,012; 5,091,652 and 4,811,218.

V. EXAMPLES

The invention will be further clarified by a consideration of the following examples, which are intended to be purely exemplary of the invention and not to in any way limit its scope. Reference numbers referring to particular compounds refer to structures provided in FIGS. 1 A–D.

Example 1

Synthesis of 1-Fluoronaphth-2-yl Boronic Acid (11)

1-fluoro naphthalene (14.61 g, 100 mmol, Aldrich Chemical) was dissolved in dry THF (50 mL) and cooled to −78° C. Then, a sec-butyl lithium solution (1.3 M in hexane, 100 mL) was added to the mixture over a period of 5 minutes. This mixture was stirred for 20 minutes at −78° C., then trimethylborate ( 15 mL, 132 mmol, Aldrich Chemical) was added. Stirring was continued at −78° C. for 15 minutes followed by stirring at room temperature for 30 minutes. The reaction was quenched by adding 100 mL of a 3:1 mixture of AcOH: $H_2O$ and stirred overnight at room temperature. Next, 500 mL of a 1:1 mixture of ethyl acetate and water was added. The organic layer was washed with 10% HCl (200 mL×1), water (200 mL×2), and brine (100 mL), dried over sodium sulfate, filtered, and solvent was removed to yield 18 grams of a white solid. This material was purified by silica-gel chromatography (350 grams of silica gel, ethyl acetate-hexane 1:1 mobile phase) to yield 16.3 g of the title compound (86%).

Example 2

Synthesis of 1,3-Dimethoxy-4-Bromo-2-Fluorobenzene (12)

2-fluoro resorcinol (prepared according to Patrick, T. B., et al., *J. Org. Chem* (1986), 51, 3242–4) (12.8 g, 100 mmol), potassium carbonate (42 g, 0.3 mol), and methyl iodide (25 mL, 0.4 mol) were mixed with acetone (300 mL) and refluxed for 6 hrs. The reaction was poured into ice-water (500 mL) and extracted in ethyl acetate (500 mL). The ethyl acetate was washed with water (200 mL×2), and brine (200 mL×1), dried over sodium sulfate, filtered, and solvent was removed to yield 14.2 grams (91%) of 1,3-dimethoxy 2-fluoro benzene. This fluoro-benzene intermediate ( 23.19 g, 148.5 mmoL), N-bromo succinimide (26.52 g, 149 mmol), and 300 uL of 70% aqueous perchloric acid (Aldrich Chemical, 3.4 mmoL) were mixed in carbon tetrachloride (100 mL) and stirred at room temperature for 1 hour. The mixture was filtered, and solvent was removed to obtain a yellow oil. The oil was subjected to silica-gel chromatography (silica gel, hexane mobile phase) to yield 33.28 grams (95%) of the 1,3-dimethoxy-4-bromo-2-fluorobenzene 12 compound as a yellow oil.

Example 3

Synthesis of 4-(Napth-2-yl)-Fluoro-1,3-Dyhydroxybenzene (14)

2-naphthylboronic acid 13 (prepared according to L. J. Diorazio et. al., *Tetrahedron*, 48, 1992, 8073) (1 g, 5.8 mmol), the 1,3-dimethoxy-4-bromo-2-fluorobenzene 12 from Example 2 (1.37 g, 5.8 mmol)), anhydrous glyme (5 mL), and tetrakis(triphenylphosphine) palladium (0) (675 mg, 0.58 mmol, Lancaster Chemical) were stirred for 15 minutes followed by the addition of potassium carbonate (1.6 g in 7 mL of water). After refluxing for 24 hrs the reaction mixture was poured into 200 mL of 1:1 10% HCl and ethylacetate. The organic layer was washed with water (100 mL×2) and brine (100 mL×1), dried over sodium sulfate, filtered, and the solvent was removed to yield 1.15 grams (71%) of the dimethylether intermediate. This intermediate (282 mg, 1 mmol) was dissolved in dry dichloromethane (5 mL) and cooled to −78° C. under argon atmosphere. After addition of 1 M boron tribromide in dichloromethane (5mL, 5 mmol), the solution was stirred at −78° C. for 30 min, then at 4° C. for 16 hrs. The reaction mixture was poured into 100 mL of ice water and extracted with ethyl acetate (100 mL). The organic layer was washed with water (100 mL×2) and brine (100 mL×1), dried over sodium sulfate, filtered, the solvent was removed, and the crude product was purified by silica-gel chromatography (silica gel, 10% $CHCl_3$ in hexane mobile phase) yielding 220 mg (86%) of solid product.

Example 4

Synthesis of 4-(Napth-2-yl)-1,3-Dihydroxybenzene (16)

This compound was prepared using essentially the same procedure as that used in Example 3 with the difference that 1,3-dimethoxy-4-bromobenzene 15 was used in place of 1,3-dimethoxy-4-bromo-2-fluorobenzene 12.

Example 5

Synthesis of 4-Phenyl-1,3-Dihydroxybenzene (18)

This compound was prepared using essentially the same procedure as that used in Example 3 with the difference that phenylboronic acid 17 (Aldrich Chemical) was used in place of 2-napthylboronic acid 13, and 1,3-dimethoxy-4-bromobenzene 15 was used in place of 1,3-dimethoxy-4-bromo-2-fluorobenzene 12.

Example 6

Synthesis of 4-(Fluoronapth-2-yl)-1,3-Dihydrox-2-fluoroybenzene (19)

This compound was prepared using essentially the same procedure as that used in Example 3 with the difference that 1-fluoronaphth-2-yl boronic acid 11 from Example 1 was used in place of 2-napthylboronic acid 13.

Example 7

Synthesis of 4-(Dibenzofuran-2-yl)-2-Fluoro-1,3-Dihydroxybenzene (22)

This compound was prepared using essentially the same procedure as that used in Example 3 with the difference that that the 2-boronic acid of 2-bromodibenzofuran (2-bromodibenzofuran was purchased from Aldrich Chemical and converted to its boronic acid 21 following the procedure of L. J. Diorazio et. al., supra) was used in place of 2-napthylboronic acid 13.

Example 8

Synthesis of Napthyl-Fluoro-Resorcinol Ketone (24)

4-(napth-2-yl)-2-fluoro-1,3-dyhydroxybenzene 14 from Example 3 (760 mg, 2.998 mmol), 2,5-dichlorotrimellitic anhydride 23 (780 mg, 2.988 mmol, PE Applied Biosystems, Foster City, Calif. (AB) part #361892), nitrobenzene (5 mL) and aluminum chloride in nitrobenzene (I 5mL, 1 M, Aldrich Chemical) were stirred at room temperature for 16 hrs. The reaction mixture was poured into a magnetically stirred mixture of ice-water (100 mL) and ethylacetate (100 mL) followed by addition of 10% HCl (100 mL) to dissolve the aluminum salts. The organic layer was washed with water (100 mL×2) and brine (100 mL×1), dried over sodium sulfate, filtered, and the solvent was removed to yield the product as a mixture of isomers. Separation by silica-gel column chromatography (silica gel, 10% methanol in dichloromethane mobile phase) yielded 340 mg (22%) of the desired slower moving isomer.

Example 9

Synthesis of Aromatic-Substituted Xanthene Dye (25)

4-(napth-2-yl)-2-fluoro-1,3-dyhydroxybenzene 14 from Example 3 (100 mg, 0.4 mmol), 2,5-dichloro trimellitic anhydride 23 (52 mg, 0.2 mmol, AB part #361892), and methane sulfonic acid (5 mL) were stirred at 120–130° C. for two hrs. The solution was cooled and mixed with ice-water (50 mL) forming a precipitate. The precipitated dye was extracted with ethyl acetate (100 mL), and the extract was washed with water (50 mL×2) and brine (50 mL×1), dried over sodium sulfate, filtered, and the solvent was removed to yield the crude dye as two isomers. The isomers were separated by preparative thick layer chromatography (slica gel, dichloromethane:methanol:acetic acid 100:10:2 by volume mobile phase) to yield 60 mg (41%) of the desired slower moving isomer.

Example 10

Synthesis of Aromatic-Substituted Xanthene Dye (26)

This compound was prepared using essentially the same procedure as that used in Example 9 with the difference that the 4-phenyl-1,3-dihydroxybenzene 18 from Example was used in place of 4-(napth-2-yl)-2-fluoro-1,3-dyhydroxybenzene 14.

Example 11

Synthesis of Aromatic-Substituted Xanthene Dye (28)

This compound was prepared using essentially the same procedure as that used in Example 9 with the difference that 1,3-dihydroxybenzofuran 27 (prepared according to Carvalho, C. F. et al., *J Chem. Soc., Perkin Trans.*, 1, 1605, (1984)) was used in place of 4-(napth-2-yl)-2-fluoro-1,3-dyhydroxybenzene 14.

Example 12

Synthesis of Aromatic-Substituted Xanthene Dye (29)

This compound was prepared using essentially the same procedure as that used in Example 9 with the difference that 4-napthyl-1,3-dihydroxybenzene 16 from Example 4 was used in place of 4-(napth-2-yl)-2-fluoro-1,3-dyhydroxybenzene 14.

Example 13

Synthesis of Aromatic-Substituted Xanthene Dye (30)

This compound was prepared using essentially the same procedure as that used in Example 9 with the difference that 4-fluoronapthyl-1,3-dihydroxybenzene 19 from Example 6 was used in place of 4-(napth-2-yl)-2-fluoro-1,3-dyhydroxybenzene 14.

Example 14

Synthesis of Aromatic-Substituted Xanthene Dye (31)

This compound was prepared using essentially the same procedure as that used in Example 9 with the difference that the 4-dibenzofuran-2-fluoro-1,3dihydroxybenzene 22 from Example 7 was used in place of 4-(napth-2-yl)-2-fluoro-1, 3-dyhydroxybenzene 14.

Example 15

Synthesis of Aromatic-Substituted Xanthene Dye (33)

4-phenyl-1,3-dihydroxybenzene 18 from Example 5 (182 mg, 1 mmol), ketone 32 (405 mg, 1 mmol, AB part #361893), and methanesulfonic acid (10 mL) were mixed and stiffed at 130–135° C. for 2 hrs. The reaction mixture was cooled, and mixed with ice water (50 mL). Precipitated dye was extracted with ethyl acetate (100 mL), and the organic layer was washed with water (50 mL×2) and brine (50 mL×1), dried over sodium sulfate, filtered, and the solvent was removed to yield the crude dye. The dye was crystallized from chloroform to yield 450 mg (81%) of pure dye.

Example 16

Synthesis of Aromatic-Substituted Xanthene Dye (35)

Dibenzofuran-1,3-diol (prepared according to Carvalho, C. F. et. Al. supra) (200 mg, 1 mmoL), 2-fluoronaphthalene-1,3-diol 34 (178 mg, 1 mmol, AB part #361828 ), and 2,5-dichloro trimellitic anhydride (260 mg, 1 mmoL, AB part# 361892) were mixed in methanesulfonic acid (10 mL) and stirred at 130–135° C. for 2 hrs. The reaction mixture was cooled and mixed with ice water (100 mL). The precipitated dye was extracted with ethyl acetate (100 mL), and the organic layer was washed with water (50 mL×2) and brine (50 mL×1), dried over sodium sulfate, filtered, and the solvent was removed to yield the crude dye as an isomeric mixture. Isomers were separated by preparative thin-layer chromatography, yielding 80 mg (13%) of dye.

Example 17

Synthesis of Aromatic-Substituted Xanthene Dye (36)

Napthyl-fluoro-resorcinol ketone 24 from Example 8 (206 mg, 0.4 mmol), and 2-fluoronaphthalene-1,3-diol 34 (72 mg, 0.4 mmol, AB part # 361828) were mixed with methane sulfonic acid (4 mL) and stirred at 120–130° C. for 2 hrs. The solution was cooled to room temperature and then poured into ice-water (100 mL). The precipitated dye was extracted with ethyl acetate (100 mL), and the organic layer was washed with water (50 mL×2) and brine (50 mL×1), dried with sodium sulfate, filtered, and the solvent was removed to yield the crude dye, which was further purified by crystallization from chloroform to yield 120mg (45%) of pure dye.

Example 18

Synthesis of a PCR Primer Labeled with Aromatic-Substituted Xanthene Dye (33)

Aromatic-substituted xanthene dye (33) from Example 15 was converted to the N-hydroxysuccinimidyl ester by reacting with 1.2 equivalents of 1-(3-dimethylaminopropyl)-3-ethylcarbodiimide hydrochloride and 1.5 equivalents of N-hydroxysuccinimide in dry DMF for 3 hrs at room temperature. The reaction mixture was mixed with 5% HCl and extracted in ethyl acetate. The extract was washed with water, dried over sodium sulfate, filtered and concentrated to a solid. The solid was dissolved in DMSO (6 mg/66 mL DMSO) forming a dye stock solution. The DMSO dye stock (5–6 mL) was added in excess (10–20×) to an aminohexyl derivatized oligonucleotide PCR primer ($1\times10^{-3}$ M) in 0.25 M bicarbonate/carbonate buffer (pH 9.4) and allowed to react for 1 hour, where the amino hexyl derivatized primer was prepared using an automated DNA synthesizer where Aminolink-2 reagent was used in the last synthesis cycle (AB p/n 400808). The dye labeled oilgonucleotide was separated from unreacted dye by passing through a Sephadex G-25 size exclusion column eluting with 0.1 molar triethylamine acetate. The fraction containing the crude labeled oligonucleotide was purified by reverse phase HPLC employing gradient elution from 8% acetonitrile in 0.1 M TEAA to 25% over 25 minutes using an RP-18 chromatography column. The pure dye labeled oligonucleotide was lyophilized to a solid. The concentration of the dye labeled oligonucleotide was determined by UV absorption at 260 nm.

Example 19

Evaluation of Relative Fluorescence Intensities of HEX and JEB Labeled PCR Primers PCR primers D19S221 and D22S423 labeled with aromatic-substituted xanthene dye (33) (JEB) according to Example 18 were compared with the same primers labeled with HEX dye using DNA from CEPH family 884, individual 15 (AM200). The target DNA was amplified according to the standard protocol for the Linkage Mapping Set, published in ABI PRISM™ Linkage Mapping Set User's Manual (AB p/n 903477 ), and evaluated for relative fluorescence intensity on an ABI PRISM™ 377 DNA Sequencer following recommended procedures. The results are summarized below in Table 1.

TABLE 1

| Dye | Primer | DNA | Size | Peak Height | Jeb/Hex Ratio |
|---|---|---|---|---|---|
|  | D22S421 |  |  |  |  |
|  |  | AM200 |  |  |  |
| Hex |  |  | 94 | 177 | 2.7 |
| Jeb |  |  | 94 | 471 |  |
| Hex |  |  | 102 | 135 | 2.8 |
| Jeb |  |  | 102 | 380 |  |
|  | D22S423 |  |  |  |  |
|  |  | AM200 |  |  |  |
| Hex |  |  | 291 | 193 | 6.0 |
| Jeb |  |  | 291 | 1165 |  |
| Hex |  |  | 307 | 77 | 6.7 |
| Jeb |  |  | 307 | 518 |  |

All publications and patent applications are herein incorporated by reference to the same extent as if each individual publication or patent application was specifically and individually indicated to be incorporated by reference.

Although only a few embodiments have been described in detail above, those having ordinary skill in the chemical arts will clearly understand that many modifications are possible in the preferred embodiment without departing from the teachings thereof. All such modifications are intended to be encompassed within the following claims.

We claim:

1. An aromatic-substituted xanthene dye compound having the formula:

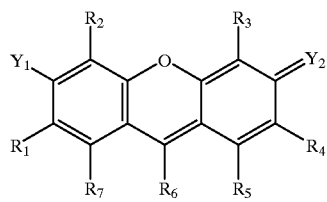

wherein:

$Y_1$ and $Y_2$ taken separately are selected from the group consisting of hydroxyl, oxygen, imminium, linking group and amine, or $Y_1$ taken together with $R_2$ is cyclic amine, or $Y_2$ taken together with $R_3$ is cyclic imine;

$R_2$, $R_3$, $R_5$, and $R_7$ taken separately are selected from the group consisting of hydrogen, fluorine, chlorine, lower alkyl, lower alkene, lower alkyne, sulfonate, sulfone, amino, imminium, amido, nitrile, lower alkoxy, phenyl, and linking group;

$R_1$ taken separately is selected from the group consisting of phenyl, substituted phenyl, polycyclic aromatic, substituted polycyclic aromatic, and electron-rich heterocycle, or when taken together with $R_7$ is selected from the group consisting of electron-rich heterocycle;

$R_4$ taken separately is selected from the group consisting of hydrogen, fluorine, chlorine, lower alkyl, lower alkene, lower alkyne, sulfonate, sulfone, amino, imminium, amido, nitrile, lower alkoxy, phenyl, linking group, amine, phenyl, substituted phenyl, polycyclic aromatic, substituted polycyclic aromatic, indene, and electron-rich heterocycle, or when taken together with $R_5$ is selected from the group consisting of phenyl, substituted phenyl, polycyclic aromatic, substituted polycyclic aromatic, indene, and electron-rich heterocycle; and $R_6$ is selected from the group consisting of acetylene, lower alkyl, lower alkene, cyano, phenyl, substituted phenyl, heterocyclic aromatic, and combinations thereof, the substituted phenyl having the structure:

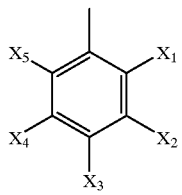

wherein:

$X_1$–$X_5$ taken separately are hydrogen, chlorine, fluorine, lower alkyl, carboxylic acid, sulfonic acid, —$CH_2OH$, or linking group.

2. The dye compound of claim 1 wherein $R_1$ taken together with $R_7$ is benzofuran having 2 and 3 positions fused to the xanthene ring.

3. The dye compound of claim 2 wherein $R_4$ taken together with $R_5$ is benzofuran having 2 and 3 positions fused to the xanthene ring.

4. The dye compound of claim 3 wherein $R_2$ and $R_3$ are hydrogen.

5. The dye compound of claim 2 wherein $R_4$ is chloro, and $R_2$ and $R_3$ are hydrogen.

6. The dye compound of claim 1 wherein $R_1$ and $R_4$ are selected from the group consisting of phenyl and substituted phenyl.

7. The dye compound of claim 6 wherein $R_2$ and RX are hydrogen, and $R_6$ is a substituted phenyl wherein $X_2$ and $X_5$ are chloro, and $X_1$ is carboxylic acid.

8. The dye compound of claim 1 wherein $R_1$ is selected from the group consisting of naphthyl and substituted naphthyl.

9. The dye compound of claim 8 wherein $R_4$ is selected from the group consisting of naphthyl and substituted naphthyl.

10. The dye compound of claim 9 wherein and $R_6$ is a substituted phenyl wherein $X_2$ and $X_5$ are chloro, and $X_1$ is carboxylic acid.

11. The dye compound of claim 10 wherein $R_2$ and $R_3$ are H.

12. The dye compound of claim 10 wherein $R_2$ and $R_3$ are fluoro.

13. The dye compound of claim 1 wherein $R_4$ taken together with $R_5$ is phenyl or polycyclic aromatic.

14. The dye compound of claim 13 wherein $R_6$ is a substituted phenyl wherein $X_2$ and $X_5$ are chloro, and $X_1$ is carboxylic acid.

15. The dye compound of claim 14 wherein $R_1$ taken together with $R_7$ is benzofuran having 2 and 3 positions fused to the xanthene ring.

16. The dye compound of claim 15 wherein $R_2$ is H and $R_3$ is fluorine.

17. The dye compound of claim 14 wherein $R_1$ is naphthyl.

18. The dye compound of claim 17 wherein $R_7$ is H and $R_2$ and $R_3$ are fluorine.

19. The dye compound of claim 1 wherein $R_1$ is phenyl, $Y_1$ is OH, $Y_2$ is O, $R_4$ is Cl, and $R_6$ is a substituted phenyl wherein $X_2$ and $X_5$ are chloro, and $X_1$ is carboxylic acid.

20. An energy transfer dye comprising:
 a donor dye capable of absorbing light at a first wavelength and emitting excitation energy in response;
 an acceptor dye capable of absorbing the excitation energy emitted by the donor dye and fluorescing at a second wavelength in response; and
 a linker for linking the donor dye and the acceptor dye, the linker serving to facilitate the efficient transfer of energy between the donor dye and the acceptor dye;
 wherein at least one of the donor dye and acceptor dye is an aromatic-substituted xanthene dye of claim 1.

21. The energy transfer dye of claim 20 wherein the linker has the structure

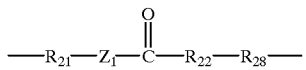

wherein
 $Z_1$ is selected from the group consisting of NH, sulfur and oxygen;
 $R_2$, is a lower alkyl attached to the donor dye;
 $R_{22}$ is a substituent selected from the group consisting of an alkene, diene, alkyne, a five and six membered ring having at least one unsaturated bond and a fused ring structure which is attached to the carbonyl carbon; and
 $R_{28}$ includes a functional group which attaches the linker to the acceptor dye.

22. The energy transfer dye of claim 21 wherein $R_{22}$ is a five or six membered ring selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene.

23. The energy transfer dye of claim 21 wherein the linker has the structure

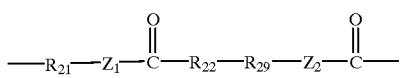

wherein
 $Z_2$ is selected from the group consisting of NH, sulfur and oxygen; and
 $R_{29}$ is a lower alkyl.

24. The energy transfer dye of claim 20 wherein the linker has the structure

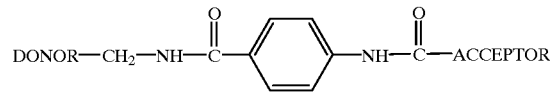

25. A labeled nucleoside/side having the formula:

NUC-DYE wherein
 NUC is a nucleoside/tide or nucleoside/tide analog;
 DYE is an aromatic-substituted xanthene dye compound of claim 1, NUC and DYE being connected by a linkage;
 wherein the linkage is attached to DYE at one of positions $R_1$–$R_6$; and
 wherein if NUC comprises a purine base, the linkage is attached to the 8-position of the purine, if NUC comprises a 7-deazapurine base, the linkage is attached to the 7-position of the 7-deazapurine, and if NUC comprises a pyrimidine base, the linkage is attached to the 5-position of the pyrimidine.

26. The labeled nucleoside/tide of claim 25 wherein NUC comprises a base selected from the group consisting of uracil, cytosine, deazaadenine, and deazaguanosine.

27. The labeled nucleoside/tide of claim 25 wherein the linkage is

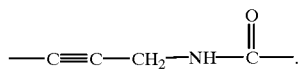

28. A phosphoramidite compound having the formula:

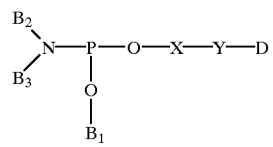

wherein:
 X is a spacer arm;
 Y is a linkage;
 $B_1$ is a phosphite ester protecting group;
 $B_2$ and $B_3$ taken separately are selected from the group consisting of lower alkyl, lower alkene, aryl, and cycloalkyl containing up to 10 carbon atoms; and
 D is a dye compound of claim 1;
 wherein Y and D are linked through a linkage attached to D at one of positions $R_1$–$R_6$.

29. The compound of claim 28 wherein $B_2$ and $B_3$ taken together form an alkene chain containing up to 5 carbon atoms in the principle chain and a total of up to 10 carbon atoms with both terminal valence bonds of said chains being attached to the nitrogen atom; or $B_2$ and $B_3$ taken together with the nitrogen atom form a saturated nitrogen heterocycle which contains one or more heteroatoms selected from the group consisting of nitrogen, oxygen, and sulfur.

30. The compound of claim 29 wherein:

$B_1$ is selected from the group consisting of methyl, β-cyanoethyl, or 4-nitrophenylethyl;

$B_2$ and $B_3$ taken separately are selected from the group consisting of isopropyl, t-butyl, isobutyl, and sec-butyl; and $B_2$ and $B_3$ taken together is morpholino.

31. The compound of claim 28 wherein X and Y taken together is

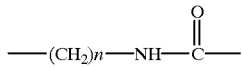

wherein n ranges from 2 to 10.

32. The compound of claim 28 wherein X and Y taken together is

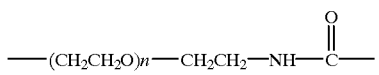

wherein n ranges from 2 to 10.

33. A phosphoramidite compound having the formula:

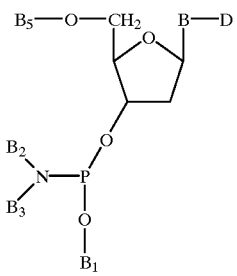

wherein:

$B_1$ is a phosphite ester protecting group;

$B_2$, and $B_3$ taken separately are selected from the group consisting of lower alkyl, lower alkene, aryl, and cycloalkyl containing up to 10 carbon atoms;

$B_5$ is an acid-cleavable hydroxyl protecting group;

B is a nucleotide base; and

D is the dye compound of claim 1;

wherein when B is purine or 7-deazapurine, the sugar moiety is attached at the $N^9$-position of the purine or 7-deazapurine, and when B is pyrimidine, the sugar moiety is attached at the $N^1$-position of the pyrimidine;

wherein B and D are linked through a linkage attached to D at one of positions $R_1$–$R_9$; and wherein if B is a purine, the linkage is attached to the 8-position of the purine, if B is 7-deazapurine, the linkage is attached to the 7-position of the 7-deazapurine, and if B is pyrimidine, the linkage is attached to the 5-position of the pyrimidine.

34. The compound of claim 33 wherein B is selected from the group consisting of uracil, cytosine, deazaadenine, and deazaguanosine.

35. A method of polynucleotide sequencing comprising the steps of:

forming a mixture of a first, a second, a third, and a fourth class of polynucleotides such that:

each polynucleotide in the first class includes a 3'-terminal dideoxyadenosine and is labeled with a first dye;

each polynucleotide in the second class includes a 3'-terminal dideoxycytidine and is labeled with a second dye;

each polynucleotide in the third class includes a 3'-terminal dideoxyguanosine and is labeled with a third dye; and each polynucleotide in the fourth class includes a 3'-terminal dideoxythymidine and is labeled with a forth dye;

wherein one of the first, second, third, or fourth dyes is an aromatic-substituted xanthene dye of claim 1;

the other of the dyes being spectrally resolvable from the asymmetric benzoxanthene dye and from each other;

electrophoretically separating the polynucleotides thereby forming bands of similarly sized polynucleotides;

illuminating the bands with an illumination beam capable of causing the dyes to fluoresce; and identifying the classes of the polynucleotides in the bands by the fluorescence spectrum of the dyes.

36. A method of fragment analysis comprising:

forming labeled polynucleotide fragments, the fragments being labeled with an aromatic-substituted xanthene dye of claim 1;

subjecting the labeled polynucleotide fragments to a size-dependent separation process; and detecting the labeled polynucleotide fragment subsequent to the separation process.

37. The method of claim 36 wherein the size-dependent separation process is electrophoresis and the labeled polynucleotide fragment is detected by fluorescence.

38. The dye compound of claim 1 in which $Y_1$ is hydroxyl and $Y_1$ is oxygen.

39. The dye compound of claim 38 in which $R_6$ is a substituted phenyl of the formula:

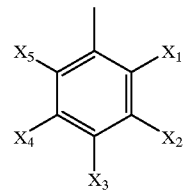

wherein $X_1$ is carboxyl; $X_2$ and $X_5$ are each chlorine; and one of $X_3$ or $X_4$ is a linking group.

40. The dye compound of claim 39 which is (Compound 25)

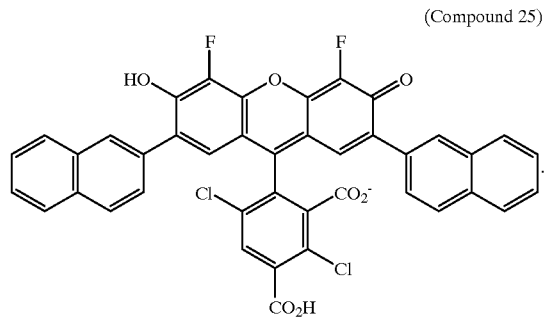

41. The dye compound of claim 39 which is
(Compound 26)
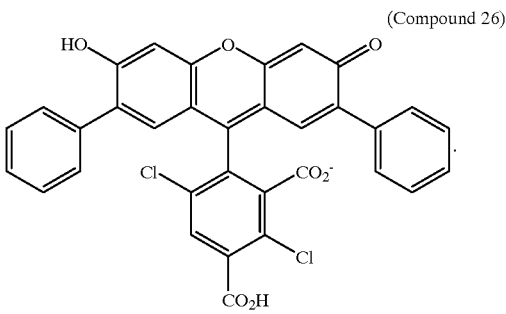
42. The compound of claim 39 which is
(Compound 28)
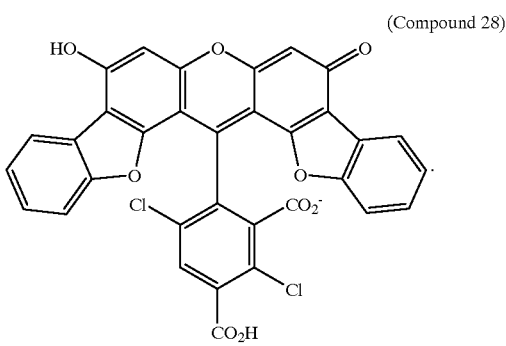
43. The compound of claim 39 which is
(Compound 29)
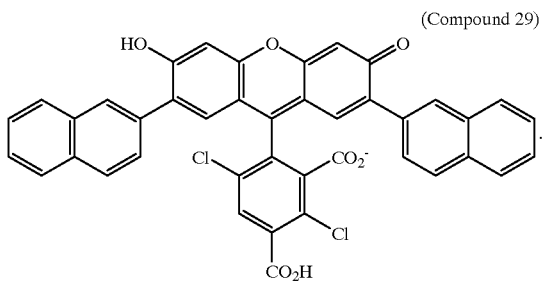
44. The compound of claim 39 which is
(Compound 30)
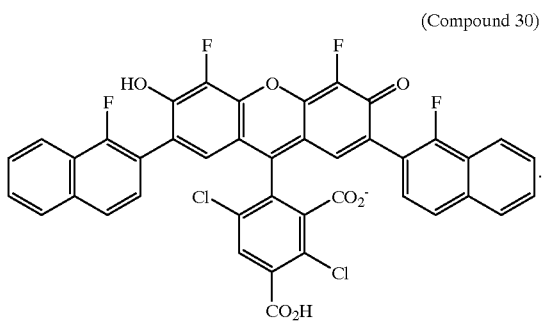
45. The compound of claim 39 which is
(Compound 31)
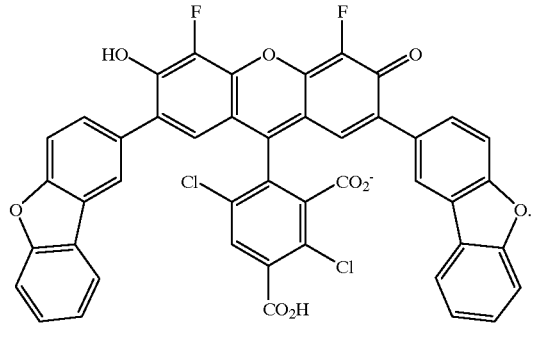
46. The compound of claim 39 which is
(Compound 33)
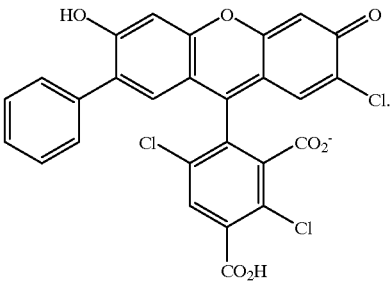
47. The compound of claim 39 which is
(Compound 35)
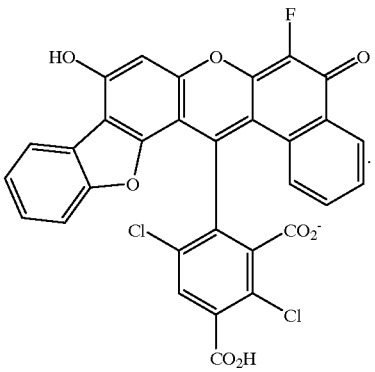
48. The compound of claim 39 which is
(Compound 36)
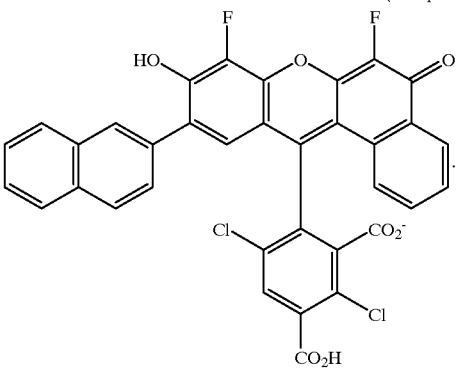
* * * * *

(12) EX PARTE REEXAMINATION CERTIFICATE (5279th)
United States Patent
Benson et al.

(10) Number: US 6,008,379 C1
(45) Certificate Issued: Feb. 28, 2006

(54) AROMATIC-SUBSTITUTED XANTHENE DYES

(75) Inventors: Scott Conrad Benson, Oakland, CA (US); Steven Michael Menchen, Fremont, CA (US); Peter David Theisen, South San Francisco, CA (US); Krishna Gajanan Upadhya, Union City, CA (US); Joan Dale Hauser, Oakland, CA (US)

(73) Assignee: Applera Corporation Applied Biosystems Group, Foster City, CA (US)

Reexamination Request:
No. 90/007,188, Sep. 1, 2004

Reexamination Certificate for:
Patent No.: 6,008,379
Issued: Dec. 28, 1999
Appl. No.: 08/942,067
Filed: Oct. 1, 1997

(51) Int. Cl.
*C07D 311/78* (2006.01)

(52) U.S. Cl. .................. 549/224; 549/218; 549/223; 536/26.6; 435/6

(58) Field of Classification Search .................. 549/218, 549/223, 224; 536/26.6; 435/6
See application file for complete search history.

(56) References Cited

U.S. PATENT DOCUMENTS

| 5,188,934 A | 2/1993 | Menchen et al. |
| 5,654,419 A | 8/1997 | Mathies et al. |
| 5,750,409 A | 5/1998 | Herrmann et al. |

FOREIGN PATENT DOCUMENTS

| EP | 0 252 683 B1 | 1/1995 |
| WO | WO 91/07507 | 5/1991 |
| WO | WO 94/05688 | 3/1994 |
| WO | WO 97/00967 | 1/1997 |

OTHER PUBLICATIONS

Golovenco, I.; Gherasimescu, E.; Moldovanu, A.; and Leonte, M. "Spectrele De Absorbtie La Unii Compusi De Fluorona," *Analele Stiint. Univ., "AL. I. Cuza" Iasi Sect. I,* 1962, 8, No. 2, 447–450.

Golovenco, I; Rusu, G. I.; Rusu, M.; Rusu, I. Gh., and Stefan, V. "Neutron Irradiation Influence on the Electrical Properties of Some Fluoron Derivatives in Thin Films," *Analele Stiint. Univ., "AL. I. Cuza" Iasi Sect. Ib,* 1972, 18, No. 1, 9–18.

Golovenco, I.; Rusu, Gh. I.; Rusu, M.; Stefan, V.; and Ciornea, D. "Gamma–Irradiation ($^{60}$Co) Influence on the Electrical Properties of Some Fluoron Derivatives in Thin Films," *Analele Stiint. Univ., "AL. I. Cuza" Iasi Sect. Ib,* 1971, 17, No. 1, 61–66.

Lee, L. G.; Connell, C. R.; Woo, S. L.; Cheng, R. D.; McArdle, B. F.; Fuller, C. W.; Halloran, N. D.; and Wilson, R. K. "DNA Sequencing with Dye–Labeled Terminators and T7 DNA Polymerase: Effect of Dyes and dNTPs on Incorporation of Dye–Terminators and Probability Analysis of Termination Fragments," *Nucleic Acids Research,* 1992, 20, No. 10, 2471–2483.

*Primary Examiner*—Amelia A. Owens

(57) ABSTRACT

A class of aromatic-substituted xanthene compounds useful as fluorescent dyes is disclosed, the compounds having the general structure

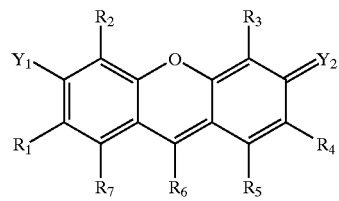

where $Y_1$ and $Y_2$ taken separately are selected from the group consisting of hydroxyl, oxygen, imminium, linking group and amine, or $Y_1$ taken together with $R_2$ is cyclic imine, or $Y_2$ taken together with $R_3$ is cyclic amine; $R_2$, $R_3$, $R_5$, and $R_7$ taken separately are selected from the group consisting of hydrogen, fluorine, chlorine, lower alkyl, lower alkene, lower alkyne, sulfonate, sulfone, amino, imminium, amido, nitrile, lower alkoxy, phenyl, and linking group; $R_1$ taken separately is selected from the group consisting of phenyl, substituted phenyl, polycyclic aromatic, substituted polycyclic aromatic, linking group and electron-rich heterocycle, or when taken together with $R_7$ is selected from the group consisting of electron-rich heterocycle and indene; $R_4$ taken separately is selected from the group consisting of amino, amido, phenyl, substituted phenyl, polycyclic aromatic, substituted polycyclic aromatic, indene, linking group and electron-rich heterocycle, or when taken together with $R_5$ is selected from the group consisting of phenyl, substituted phenyl, polycyclic aromatic, substituted polycyclic aromatic, indene, and electron-rich heterocycle; and $R_6$ is selected from the group consisting of acetylene, lower alkyl, lower alkene, cyano, phenyl, substituted phenyl, and heterocyclic aromatic. In another aspect, the invention includes methods for synthesizing the above dye compounds and intermediates. In yet another aspect, the present invention includes reagents labeled with the [asymmetric benzoxanthene dye] *aromatic-substituted xanthene* compounds, including deoxynucleotides, dideoxynucleotides, phosphoramidites, and polynucleotides. In an additional aspect, the invention includes methods utilizing such dye compounds and reagents including dideoxy polynucleotide sequencing and fragment analysis methods.

US 6,008,379 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 20–34 is confirmed.

Claims 1, 7, 10, 14, 19, 35, 38 and 39 are determined to be patentable as amended.

Claims 2–6, 8, 9, 11–13, 15–18, 36, 37 and 40–48, dependent on an amended claim, are determined to be patentable.

1. An aromatic-substituted xanthene dye compound having the formula:

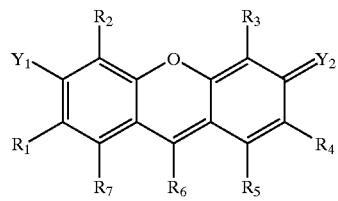

wherein:
$Y_1$ and $Y_2$ taken separately are selected from the group consisting of hydroxyl, oxygen, imminium, linking group and amine, or $Y_1$ taken together with $R_2$ is cyclic amine, or $Y_2$ taken together with $R_3$ is cyclic imine;

$R_2$, $R_3$, $R_5$, and $R_7$ taken separately are selected from the group consisting of hydrogen, fluorine, chlorine, lower alkyl, lower alkene, lower alkyne, sulfonate, sulfone, amino, imminium, amido, nitrile, lower alkoxy, phenyl, and linking group;

$R_1$ taken separately is selected from the group consisting of phenyl, substituted phenyl, polycyclic aromatic, substituted polycyclic aromatic, and electron-rich heterocycle, or when taken together with $R_7$ is selected from the group consisting of electron-rich heterocycle;

$R_4$ taken separately is selected from the group consisting of hydrogen, fluorine, chlorine, lower alkyl, lower alkene, lower alkyne, sulfonate, sulfone, amino, imminium, amido, nitrile, lower alkoxy, phenyl, linking group, amine, phenyl, substituted phenyl, polycyclic aromatic, substituted polycyclic aromatic, indene, and electron-rich heterocycle, or when taken together with $R_5$ is selected from the group consisting of phenyl, substituted phenyl, polycyclic aromatic, substituted polycyclic aromatic, indene, and electron-rich heterocycle; and $R_6$ is [selected from the group consisting of acetylene, lower alkyl, lower alkene, cyano, phenyl, substituted phenyl, heterocyclic aromatic, and combinations thereof, the] *a* substituted phenyl having the structure:

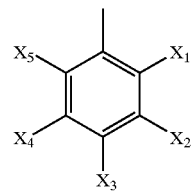

wherein:

*$X_2$ and $X_5$ are each chlorine; and*

[$X_1$–$X_5$] *$X_1$, $X_3$, and $X_4$* taken separately are hydrogen, chlorine, fluorine, lower alkyl, carboxylic acid, sulfonic acid, —CH$_2$OH, or linking group.

7. The dye compound of claim 6 wherein $R_2$ and [RX] *$R_7$* are hydrogen, [and $R_6$ is a substituted phenyl wherein $X_2$ and $X_5$ are chloro,] and $X_1$ is carboxylic acid.

10. The dye compound of claim 9 wherein [and $R_6$ is a substituted phenyl wherein $X_2$ and $X_5$ are chloro, and] $X_1$ is carboxylic acid.

14. The dye compound of claim 13 wherein [$R_6$ is a substituted phenyl wherein $X_2$ and $X_5$ are chloro, and] $X_1$ is carboxylic acid.

19. The dye compound of claim 1 wherein $R_1$ is phenyl, $Y_1$ is OH, $Y_2$ is O, $R_4$ is Cl, and [$R_6$ is a substituted phenyl wherein $X_2$ and $X_5$ are chloro, and] $X_1$ is carboxylic acid.

35. A method of polynucleotide sequencing comprising the steps of:

forming a mixture of a first, a second, a third, and a fourth class of polynucleotides such that:

each polynucleotide in the first class includes a 3'-terminal dideoxyadenosine and is labeled with a first dye;

each polynucleotide in the second class includes a 3'-terminal dideoxycytidine and is labeled with a second dye;

each polynucleotide in the third class includes a 3'-terminal dideoxyguanosine and is labeled with a third dye; and each polynucleotide in the fourth class includes a 3'-terminal dideoxythymidine and is labeled with a forth dye;

wherein one of the first, second, third, or fourth dyes is an aromatic-substituted xanthene dye of claim 1;

the other of the dyes being spectrally resolvable from the [asymmetric benzoxanthene] *aromatic-substituted xanthene* dye and from each other;

electrophoretically separating the polynucleotides thereby forming bands of similarly sized polynucleotides;

illuminating the bands with an illumination beam capable of causing the dyes to fluoresce; and identifying the classes of the polynucleotides in the bands by the fluorescence spectrum of the dyes.

38. The dye compound of claim 1 in which $Y_1$ is hydroxyl and [$Y_1$] $Y_2$ is oxygen.

39. The dye compound of claim 38 [in which $R_6$ is a substituted phenyl of the formula:

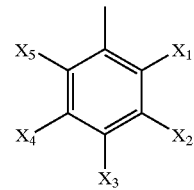

]
wherein $X_1$ is carboxyl; [$X_2$ and $X_5$ are each chlorine;] and one of $X_3$ or $X_4$ is a linking group.

* * * * *